United States Patent [19]

Cooper

[11] Patent Number: 4,794,112

[45] Date of Patent: Dec. 27, 1988

[54] ACETAMINOPHEN/HYDROXYZINE ANALGESIC COMBINATIONS

[76] Inventor: Stephen A. Cooper, 85 Westview Rd., Short Hills, N.J. 07078

[21] Appl. No.: 829,571

[22] Filed: Feb. 14, 1986

Related U.S. Application Data

[63] Continuation of Ser. No. 753,014, Jul. 8, 1985, abandoned, which is a continuation of Ser. No. 586,567, Mar. 6, 1984, abandoned, which is a continuation-in-part of Ser. No. 448,290, Dec. 9, 1982.

[51] Int. Cl.$^4$ .................. A61K 31/16; A61K 31/495
[52] U.S. Cl. ..................................... 514/255; 514/629
[58] Field of Search ............................... 514/255, 629

Primary Examiner—Stanley J. Friedman
Attorney, Agent, or Firm—Caesar, Rivise, Bernstein, Cohen & Pokotilow, Ltd.

[57] ABSTRACT

Combinations of hydroxyzine or it's therapeutically acceptable, non-toxic salts, with acetaminophen are effective analgesic compositions.

20 Claims, No Drawings

ACETAMINOPHEN/HYDROXYZINE ANALGESIC COMBINATIONS

"This application is a continuation of Ser. No. 753,014 filed July 8, 1985, which is a continuation of Ser. No. 586,567, filed Mar. 6, 1984, which is a continuation-in-part of Ser. No. 448,290, filed Dec. 9, 1982, all are now abandoned".

The present invention relates to analgesic compositions and more particularly to new analgesic combinations comprising 1-(p-chlorobenzhydryl)-4-[2-(2-hydroxyethoxy)ethyl]diethylenediamine or a therapeutically acceptable, nontoxic organic acid or a mineral acid addition salt thereof in combination with acetaminophen. The present invention also relates to a method for alleviating pain using the aforementioned analgesic combinations.

BACKGROUND OF THE INVENTION

The compound 1-(p-chlorobenzhydryl)-4-[2-(2-hydroxyethoxy)ethyl]-diethylenediamine (referred to generically as hydroxyzine) and its salt derivatives are known to be effective tranquilizers (see U.S. Pat. No. 2,899,436). Acetaminophen is a well known analgesic agent.

The search for analgesic agents of all kinds which will optimize the therapeutic effect and minimize undesired effects has been a long continuing quest in the attempt to find improved treatments. This search has included coadministrations involving analgesics, one with another or with a drug of another type. Among the wide variety of combined administrations which have been considered are those involving a tranquilizer and an analgesic. Such combinations have been mainly of interest in situations where both stress and great pain are anticipated or experienced, such as in surgical situations and the advanced stages of diseases such as cancer. For example, the literature reveals a number of clinical evaluations of the combination of hydroxyzine and a narcotic analgesic, generally co-administered by the i.v. or intramuscular routes, but the results in terms of analgesia have been largely judged to be additive.

SUMMARY OF THE INVENTION

It has now surprisingly been found that co-administration of hydroxyzine and acid salts thereof with acetaminophen has an especially advantageous effect in alleviating pain in human subjects. The invention is practised by administration adapted to achieve absorption through the alimentary canal, i.e. by oral or rectal administration, desirably by oral administration. The invention also provides pharmaceutical compositions for oral or rectal administration comprising: (a) acetaminophen, (b) hydroxyzine in free base form or in pharmaceutically acceptable acid addition salt form, and (c) a pharmaceutically acceptable carrier.

DETAILED DESCRIPTION OF THE INVENTION

In accordance with the present invention, pain is relieved in human subjects by co-administering thereto orally or rectally; (a) acetaminophen and (b) hydroxyzine or an acid salt form thereof in an amount sufficient to potentiate the analgesic action of component (a); the total amount of components (a) and (b) being an amount sufficient to relieve pain.

Pharmaceutical compositions which are also provided by the present invention are adapted for oral or rectal administration and comprise a pain relieving effective amount of the combination of: (a) acetaminophen, (b) hydroxyzine or an acid salt form thereof in an amount sufficient to potentiate the analgesic action of component (a), and (c) a pharmaceutically acceptable carrier. This mixture is an effective general purpose analgesic and is desirably free of narcotic constituents.

The amounts of hydroxyzine per dose to be employed in practicing the invention may be similar to those conventionally employed in using hydroxyzine as a tranquilizer, and generally will not exceed about 120 milligrams. At such levels my clinical investigations confirm that hydroxyzine is essentially inactive orally as an analgesic. Hence, the action of hydroxyzine in the present invention has been surprisingly found to be a synergism of the potentiating type. Preferably, the amount of hydroxyzine will not exceed 100 mg. per dose. In general, at least about 25 milligrams of hydroxyzine and its acid salts will be administered per dose in order to potentiate the analgesic effect of acetaminophen. Preferably, at least 50 mg. and typically at least about 70 mg. of hydroxyzine will be administered per dose. Hence, a dose range for each administration of hydroxyzine and its salts may be from 25 mg. to 120 mg., more usually 25 mg. to 100 mg., preferably 50 mg. to 100 mg. and typically 70 mg. to 100 mg. The weighted dose amounts of hydroxyzine and its salts as referred to herein are on the equivalent basis of hydroxyzine dihydrochloride. The hydroxyzine is preferably employed in acid addition salt form, e.g. the dihydrochloride or pamoate.

The precise therapeutic dose of the individual components as well as the instantly disclosed combinations thereof may vary with the kind of pharmaceutic process, severity of the condition, administration schedule and other known factors, and doses typically continued until the condition causing the pain is ameliorated. With regard to acetaminophen, it will be co-administered with the pain relieving potentiating effective amount of hydroxyzine (or its acid salts), in a total combined pain relieving effective amount, in doses given 3 to 6 times a day as needed to relieve pain. In general, it is desirable to employ at least an amount of the acetaminophen that would by itself be minimally effective clinically in the adult human to produce analgesia. Suitable per dose amounts for acetaminophen are from 200 milligrams to 1,300 milligrams, but are preferably from 300 mg to 650 mg.

In Table I, below, there are the general (a) and preferred (b) dose ranges of acetaminophen (column A); the weight ratio thereto of hydroxyzine when the hydroxyzine dose to be administered is within the range of 25 to 100 mg (Column B); and the weight ratio thereto of hydroxyzine when the hydroxyzine dose to be administered is within the range of 50 to 100 mg (Column C.).

TABLE I

| Column A Acetaminophen dose range | Column B Weight ratio hydroxyzine range at 25–100 mg. to acetaminophen dose range | Column C Weight ratio hydroxyzine range at 50–100 mg to acetaminophen dose range |
| --- | --- | --- |
| (a) 200–1300 | 1:52 to 1:2 | 1:26 to 1:2 |
| (b) 300–650 | 1:26 to 1:3 | 1:13 to 1:3 |

The limits of weight ratio ranges of hydroxyzine for the hydroxyzine dose ranges of 25 to 120 mg. and 70 to 100 mg. to the dose ranges for acetaminophen given in Table I may be readily calculated from the dose ranges given in Column A of Table I for acetaminophen and such weight ratio ranges are also deemed disclosed herein. It will be evident that the weight ratio ranges of hydroxyzine to acetaminophen as indicated above may be used to formulate pharmaceutical compositions in accordance with the invention, provided that an acetaminophen pain relieving potentiating effective amount of hydroxyzine is included.

The usefulness of the combinations of the present invention and the ability of hydroxyzine to potentiate the pain relieving properties of acetaminophen have been demonstrated in the following representative clinical trial in humans.

A clinical test was conducted involving subjects who were outpatients undergoing the surgical removal of impacted teeth. After surgery was completed, the patients were given one dose of a medication and a questionnaire. They were asked to take the medication when their post-operative pain reached moderate to severe intensity. They were instructed to record their starting pain level in numerical fashion, i.e., moderate (2) or severe (3) and then at each hour for the next four hours to record their pain intensity as severe (3), moderate (2), slight (1), or none (0); and their relief from the starting pain as complete (4), a lot (3), some (2), a little (1) or none (0). The procedure employed is state-of-the-art methodology and is described in more detail in an article entitled "A Model to Evaluate Mild Analgesics in Oral Surgery Out-patients", S. A. Cooper and W. T. Beaver, Clinical Pharmacology and Therapeutics, Vol., 20, Number 2, pp. 241–250, August, 1976.

In the test, the patients were given a placebo, 600 milligrams of acetaminophen, 100 milligrams of Hydroxyzine pamoate, or a mixture of 100 milligrams of Hydroxyzine pamoate and 600 milligrams of acetaminophen. The results of the test are recorded in Table 1, below. Pain intensity difference scores were derived by subtracting the pain level at each hour after ingestion from the intensity at the time of initial administration. Hence if the patient's pain was judged to be "moderate" (value of 2) at the start of the test and the patient judged his pain to be "slight" at hours one, two, three and four (assigned value of 1), the pain intensity difference score would be 4, that is 2 minus 1 or plus 1 at each of the four hourly measuring points. Pain relief scores for each pain estimate were assigned according to patient's hourly estimate of relief. Accordingly, if the patient recorded a little relief at hour one (a score of 1), some relief at hour two (a score of 2) and a lot of relief at hours three and four (score 3 for each hour) his pain relief score would be 9.

TABLE 1

|  | Placebo | Acetaminophen 600 mg | Hydroxyzine Pamoate 100 mg | Hydroxyzine 100 mg. + Acetaminophen 600 mg |
|---|---|---|---|---|
| Number of Patients | 6 | 7 | 4 | 6 |
| Mean Sum Pain Intensity Difference Score | −0.17 | 3.14 | −0.50 | 4.50 |
| Mean Sum Pain Relief Score | 4.00 | 8.14 | 3.00 | 10.83 |

Thus the above test indicates a synergism of the potentiating kind for the combination of hydroxyzine and acetaminophen, and that the combination is thus indicated as particularly useful in alleviating pain. The test also confirms that hydroxyzine alone is inactive orally as an analgesic. Similar results indicating the acetaminophen pain relieving potentiation ability are also obtained when repeating the above clinical test with the combination of 600 milligrams of acetaminophen and 50 milligrams of hydroxyzine and with the combination of 350 milligrams of acetaminophen and 100 milligrams of hydroxyzine.

The pharmaceutical compositions according to the invention suitably contain pharmaceutically acceptable carriers which are admixed with the active agent components (a) and (b). Such compositions may be prepared from conventional, materials by procedures well known in the art. The compositions of this invention may be adapted for oral administration and administration through the rectum. Forms suitable for oral administration are for example tablets, dispersible powders, granules, capsules, syrups, elixirs or suspensions. Compositions for oral use contain one or more conventional adjuvants, such as sweetening agents flavoring agents, coloring agents and preserving agents, in order to provide an elegant and palatable preparation. Tablets may contain the active ingredients in admixture with conventional pharmaceutically acceptable excipients, e.g. inert carriers, such as calcium carbonate, sodium carbonate, lactose, and talc, granulating and disintegrating agents, e.g. starch and aligninic acid, binding agents, e.g. starch gelatin and acacia, and lubricating agents, e.g. magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredients in admixture with any of the conventional excipients utilized in the preparation of such compositions, e.g. suspending agents such as methyl-cellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredients alone or admixed with an inert solid carrier, e.g. calcium carbonate, calcium phosphate and kaolin. These pharmaceutical compositions may contain up to about 90% of the active ingredients in combination with the carrier or adjuvant. Preferably the compositions are put up in unit dosage form particularly in unit dosage form for oral administration, e.g. tablets or capsules. Such forms may contain the active ingredients separately, e.g. in separate layers in a layer or mantle tablet or in split capsules. Oral administration is preferred.

Conveniently the active agents will be administered in fixed combinations having e.g. the individual dosages outlined above and in unit dosage form.

They can be administered e.g. in sustained release form or in divided doses 2 to 4 times a day or as indicated by the condition to be treated e.g. 3 to 6 times as needed to relieve pain.

The active agents (a) and (b) can also be administered in the indicated dosages individually and concomitantly.

The following Example is illustrative of compositions for use in the invention.

EXAMPLE A

A No. 1 capsule containing the ingredients indicated below may be prepared by conventional techniques and administered at a dose of 1 or 2 capsules 4 to 6 times a day to relieve pain.

| Ingredient | Weight (mg) |
|---|---|
| Acetaminophen | 325 |
| Hydroxyzine pamoate | 50 |
| Corn starch | 150 |
| Magnesium stearate | 2 |

What is claimed is:

1. A pharmaceutical composition for oral or rectal administration to a human subject, said composition comprising a pharmaceutically acceptable carrier and a pain relieving effective amount of the combination of (a) at least 200 mg. to 1300 mg. of acetaminophen and (b) at least 25 mg. to 120 mg. of hydroxyzine or an acid salt form thereof in an amount sufficient to potentiate the analgesic action of acetaminophen.

2. A composition in accord with claim 1 in which acetaminophen is present in at least an amount which by itself would be minimally effective clinically to produce analgesia in a adult human.

3. A composition in accord with claim 2 in which the weight ratio of component (b) to acetaminophen is within the range of from 1:52 to 1:2.

4. A composition in accord with claim 3 in which the weight ratio of component (b) to acetaminophen is within the range of from 1:26 to 1:3.

5. A composition in accord with claim 3 in which the weight ratio of component (b) to acetaminophen is within the range of from 1:13 to 1:3.

6. A composition in accord with claim 1 in which the component (b) is present in an amount of from 25 to 100 milligrams.

7. A composition in accord with claim 3 in which the component (b) is present in an amount of from 25 to 100 milligrams.

8. A composition in accord with claim 4 in which the component (b) is present in an amount of from 25 to 100 milligrams.

9. A composition in accord with claim 1 in which the component (b) is present in an amount of from 25 to 100 milligrams and acetaminophen is present in an amount from 300 to 650 milligrams.

10. A composition in accord with claim 5 in which the component (b) is present in an amount of from 50 to 100 milligrams and acetaminophen is present in an amount from 300 to 650 milligrams.

11. The method of relieving pain in a human subject, said method comprising orally or rectally co-administering to said subject; (a) at least 200 mg. to 1300 mg. of acetaminophen and (b) at least 25 mg. to 120 mg. of hydroxyzine or an acid salt form thereof in an amount sufficient to potentiate the analgesic action of acetaminophen; said acetaminophen and component (b) being co-administered in a total pain relieving effective amount.

12. The method of claim 11 in which the acetaminophen is administered in at least an amount which by itself would be minimally effective clinically to produce analgesia in a adult human.

13. The method of claim 12 in which the weight ratio of component (b) to acetaminophen is within the range of from 1:52 to 1:2.

14. The method of claim 13 in which the weight ratio of component (b) to acetaminophen is within the range of from 1:26 to 1:3.

15. The method of claim 13 in which the weight ratio of component (b) to acetaminophen is within the range of from 1:13 to 1:3.

16. The method of claim 11 in which the component (b) is administered in an amount of from 25 to 100 milligrams.

17. The method of claim 13 in which the component (b) is administered in an amount of from 25 to 100 milligrams.

18. The method of claim 15 in which the component (b) is administered in an amount of from 50 to 100 milligrams.

19. The method of claim 11 in which the component (b) is administered in an amount of from 25 to 100 milligrams and acetaminophen is administered in an amount of from 300 to 650 milligrams.

20. The method of claim 15 in which the component (b) is administered in an amount of from 50 to 100 milligrams and acetaminophen is administered in an amount from 300 to 650 milligrams.

* * * * *